US006909028B1

(12) United States Patent
Shawver et al.

(10) Patent No.: US 6,909,028 B1
(45) Date of Patent: *Jun. 21, 2005

(54) STABLE BREATHABLE ELASTIC GARMENTS

(75) Inventors: Susan Elaine Shawver, Roswell, GA (US); Paul Windsor Estey, Cumming, GA (US); William Bela Haffner, Kennesaw, GA (US); Cindy Janja Blackstock, Cumming, GA (US); Glynis Allicia Walton, Roswell, GA (US); Duane Girard Uitenbroek, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/122,326

(22) Filed: Jul. 24, 1998

Related U.S. Application Data

(60) Provisional application No. 60/059,001, filed on Sep. 17, 1997.

(51) Int. Cl.[7] .................................................. A61F 13/15
(52) U.S. Cl. ..................... 604/370; 604/358; 604/365; 604/366; 604/367; 604/385.1; 604/383; 428/283; 428/284; 428/198
(58) Field of Search .......................... 428/283, 284, 428/198; 604/385.2, 385.1, 358, 365, 366, 367, 383

(56) References Cited

U.S. PATENT DOCUMENTS

| 2,527,299 A | 10/1950 | DePhillips .................... 154/50 |
| 3,276,944 A | 10/1966 | Levy ........................... 161/150 |
| 3,338,992 A | 8/1967 | Kinney .......................... 264/24 |
| 3,341,394 A | 9/1967 | Kinney .......................... 161/72 |
| 3,502,538 A | 3/1970 | Peterson ...................... 161/150 |
| 3,502,763 A | 3/1970 | Hartman ....................... 264/210 |
| 3,510,344 A | 5/1970 | Dunderdale ................... 117/76 |
| 3,542,615 A | 11/1970 | Dobo et al. .................. 156/181 |
| 3,645,992 A | 2/1972 | Elston ....................... 260/80.78 |
| 3,676,242 A | 7/1972 | Prentice ..................... 156/62.4 |
| 3,692,618 A | 9/1972 | Dorschner et al. ............ 161/72 |
| 3,802,817 A | 4/1974 | Matsuki et al. ............... 425/66 |
| 3,836,423 A | 9/1974 | Wagner et al. .............. 161/159 |
| 3,849,241 A | 11/1974 | Butin et al. ................. 161/169 |
| 3,894,904 A | 7/1975 | Cook .......................... 156/229 |

(Continued)

FOREIGN PATENT DOCUMENTS

| CA | 803 714 | 1/1969 |
| DE | 3 724 510 | 2/1989 |
| EP | 0 061 238 | 9/1982 |

(Continued)

OTHER PUBLICATIONS

Japanese Abstract 50–076187, Jun. 21, 1975.
Japanese Abstract 54–038–344A, Sep. 2, 1977.
Japanese Abstract 10–794249A, Sep. 19, 1987.

(Continued)

*Primary Examiner*—John G. Weiss
*Assistant Examiner*—Linh Truong
(74) *Attorney, Agent, or Firm*—Steven D. Flack

(57) ABSTRACT

A thermally stable microporous breathable film is provided comprising at least 35% filler, by weight of the filled-film, and a thermoplastic polymer blend of a first polyethylene polymer and a second polyethylene polymer. The first polyethylene polymer comprises 30%–70% by weight of the polymer blend and can have a density between about 0.86 g/cm³ and 0.89 g/cm³ and the second polyethylene polymer can have a density between about 0.90 g/cm³ and 0.92 g/cm³. The filled-film can be uniaxially or biaxially oriented to form a microporous film and/or film laminate having good body conformance and which retains a high WVTR at 37° C. and above.

34 Claims, 3 Drawing Sheets

U.S. PATENT DOCUMENTS

| | | | |
|---|---|---|---|
| 3,973,063 A | 8/1976 | Clayton | 428/35 |
| 4,041,203 A | 8/1977 | Brock et al. | 428/157 |
| 4,087,486 A | 5/1978 | Fielding et al. | 260/897 A |
| 4,104,404 A | 8/1978 | Bieler et al. | 428/35 |
| 4,110,414 A * | 8/1978 | Lindsay et al. | 260/897 |
| 4,136,501 A | 1/1979 | Connolly | 53/461 |
| 4,147,827 A | 4/1979 | Breidt, Jr. et al. | 428/218 |
| 4,154,885 A | 5/1979 | Tecl et al. | 428/198 |
| 4,178,401 A | 12/1979 | Weinberg et al. | 428/35 |
| 4,185,135 A | 1/1980 | Huff | 428/96 |
| 4,190,624 A | 2/1980 | Alard et al. | 264/146 |
| 4,194,041 A | 3/1980 | Gore et al. | 428/315 |
| 4,196,240 A | 4/1980 | Lustig et al. | 428/35 |
| 4,197,150 A | 4/1980 | Breidt, Jr. et al. | 156/229 |
| 4,239,826 A | 12/1980 | Knott, II et al. | 428/35 |
| 4,252,851 A | 2/1981 | Lansbury et al. | 428/336 |
| 4,254,175 A | 3/1981 | Kubat et al. | 428/213 |
| 4,265,954 A | 5/1981 | Romanek | 428/85 |
| 4,275,119 A | 6/1981 | Weiner | 428/516 |
| 4,276,330 A | 6/1981 | Stanley et al. | 428/35 |
| 4,289,832 A | 9/1981 | Schwarz | 428/542 |
| 4,294,889 A | 10/1981 | Hashimoto | 428/515 |
| 4,296,156 A | 10/1981 | Lustig et al. | 428/35 |
| 4,297,408 A | 10/1981 | Stead et al. | 428/240 |
| 4,303,708 A | 12/1981 | Gebhardt et al. | 428/35 |
| 4,306,559 A | 12/1981 | Nishizawa et al. | 128/287 |
| 4,312,964 A | 1/1982 | Sekine et al. | 525/88 |
| 4,332,845 A | 6/1982 | Nawata et al. | 428/35 |
| 4,339,495 A | 7/1982 | Weiner | 428/349 |
| 4,340,563 A | 7/1982 | Appel et al. | 264/518 |
| 4,340,641 A | 7/1982 | Weiner | 428/349 |
| 4,341,216 A | 7/1982 | Obenour | 128/287 |
| 4,343,848 A | 8/1982 | Leonard, Jr. | 428/156 |
| 4,344,999 A | 8/1982 | Gohlke | 428/212 |
| 4,347,844 A | 9/1982 | Ohki et al. | 128/287 |
| 4,350,655 A | 9/1982 | Hoge | 264/145 |
| 4,352,849 A | 10/1982 | Mueller | 428/213 |
| 4,353,945 A | 10/1982 | Sampson | 428/90 |
| 4,364,985 A | 12/1982 | Tokuyama et al. | 428/149 |
| RE31,191 E | 3/1983 | Connolly | 206/386 |
| 4,376,147 A | 3/1983 | Byrne et al. | 428/167 |
| 4,377,616 A | 3/1983 | Ashcraft et al. | 428/213 |
| 4,384,024 A | 5/1983 | Mitchell et al. | 428/349 |
| 4,386,129 A | 5/1983 | Jacoby | 428/215 |
| 4,390,385 A | 6/1983 | Ferguson et al. | 156/229 |
| 4,399,173 A | 8/1983 | Anthony et al. | 428/35 |
| 4,407,879 A | 10/1983 | Smart | 428/141 |
| 4,407,986 A | 10/1983 | Nomura et al. | 523/200 |
| 4,430,468 A | 2/1984 | Schumacher | 524/109 |
| 4,433,026 A | 2/1984 | Molde | 428/252 |
| 4,434,258 A | 2/1984 | Schumacher et al. | 524/13 |
| 4,438,175 A | 3/1984 | Ashcraft et al. | 428/315.5 |
| 4,439,478 A | 3/1984 | Ferguson et al. | 428/137 |
| 4,443,511 A | 4/1984 | Worden et al. | 428/198 |
| 4,494,629 A | 1/1985 | Raeburn | 188/65.5 |
| 4,501,797 A | 2/1985 | Super et al. | 428/349 |
| 4,522,203 A | 6/1985 | Mays | 128/132 D |
| 4,525,407 A | 6/1985 | Ness | 428/138 |
| 4,533,509 A | 8/1985 | Gust et al. | 264/171 |
| 4,533,602 A | 8/1985 | Nakamura et al. | 428/447 |
| 4,546,029 A | 10/1985 | Cancio et al. | 428/141 |
| 4,552,714 A | 11/1985 | Krueger et al. | 264/171 |
| 4,560,598 A | 12/1985 | Cowan | 428/35 |
| 4,582,752 A | 4/1986 | Duncan | 428/317.9 |
| 4,582,753 A | 4/1986 | Duncan | 428/317.9 |
| 4,585,604 A | 4/1986 | Okuyama et al. | 264/41 |
| 4,595,629 A | 6/1986 | Mays | 428/286 |
| 4,603,174 A | 7/1986 | Okada et al. | 525/240 |
| 4,606,970 A | 8/1986 | Sharps, Jr. | 428/301 |
| 4,613,643 A | 9/1986 | Nakamura et al. | 524/426 |
| 4,615,922 A | 10/1986 | Newsome et al. | 428/35 |
| 4,636,424 A | 1/1987 | Amemiya et al. | 428/198 |
| 4,672,091 A | 6/1987 | Berta | 525/88 |
| 4,681,578 A | 7/1987 | Anderson et al. | 604/385 |
| 4,681,793 A | 7/1987 | Linman et al. | 428/138 |
| 4,684,568 A | 8/1987 | Lou | 428/265 |
| 4,686,257 A | 8/1987 | Mitsuno et al. | 524/449 |
| 4,690,679 A | 9/1987 | Mattingly, III et al. | 604/383 |
| 4,698,372 A | 10/1987 | Moss | 521/145 |
| 4,702,954 A | 10/1987 | Duncan | 428/213 |
| 4,704,238 A | 11/1987 | Okuyama et al. | 264/41 |
| 4,704,323 A | 11/1987 | Duncan et al. | 428/286 |
| 4,705,813 A | 11/1987 | Ito et al. | 521/92 |
| 4,713,133 A | 12/1987 | Kent | 156/162 |
| 4,725,481 A | 2/1988 | Ostapchenko | 428/213 |
| 4,734,324 A | 3/1988 | Hill | 428/317.3 |
| 4,748,070 A | 5/1988 | Beehler | 428/198 |
| 4,758,396 A | 7/1988 | Crass et al. | 264/145 |
| 4,758,462 A | 7/1988 | Park et al. | 428/213 |
| 4,761,324 A | 8/1988 | Rautenberg et al. | 428/198 |
| 4,777,073 A | 10/1988 | Sheth | 428/155 |
| 4,780,364 A | 10/1988 | Wade et al. | 428/315.5 |
| 4,791,144 A | 12/1988 | Nagou et al. | 521/90 |
| 4,795,768 A | 1/1989 | Ancker et al. | 523/200 |
| 4,803,035 A | 2/1989 | Kresge et al. | 264/519 |
| 4,806,411 A | 2/1989 | Mattingly, III et al. | 428/139 |
| 4,814,124 A | 3/1989 | Aoyama et al. | 264/41 |
| 4,815,714 A | 3/1989 | Douglas | 264/22 |
| 4,816,328 A | 3/1989 | Saville et al. | 428/246 |
| 4,820,471 A | 4/1989 | van der Molen | 264/564 |
| 4,824,718 A | 4/1989 | Hwang | 428/284 |
| 4,824,912 A | 4/1989 | Su | 525/240 |
| 4,829,096 A | 5/1989 | Kitamura et al. | 521/79 |
| 4,832,886 A | 5/1989 | Douglas | 264/41 |
| 4,833,026 A | 5/1989 | Kausch | 428/315.5 |
| 4,842,741 A | 6/1989 | Coughlin et al. | 210/500.36 |
| 4,842,794 A | 6/1989 | Hovis et al. | 264/145 |
| 4,857,370 A | 8/1989 | Overbergh et al. | 422/34.9 |
| 4,861,652 A | 8/1989 | Lippert et al. | 428/284 |
| 4,863,792 A | 9/1989 | Mirozinski | 428/315.5 |
| 4,879,078 A | 11/1989 | Antoon, Jr. | 264/41 |
| 4,902,553 A | 2/1990 | Hwang et al. | 428/156 |
| 4,908,251 A | 3/1990 | Imura et al. | 428/68 |
| 4,909,971 A | 3/1990 | Coughlin et al. | 264/45.5 |
| 4,910,639 A | 3/1990 | Schloegl et al. | 361/323 |
| 4,921,652 A | 5/1990 | Tsuji et al. | 264/41 |
| 4,921,653 A | 5/1990 | Aoyama et al. | 264/41 |
| 4,923,650 A | 5/1990 | Antoon, Jr. et al. | 264/41 |
| 4,929,303 A | 5/1990 | Sheth | 156/209 |
| 4,935,287 A | 6/1990 | Johnson et al. | 428/198 |
| 4,957,943 A | 9/1990 | McAllister et al. | 521/64 |
| 4,960,637 A | 10/1990 | Biczenczuk | 428/314.4 |
| 4,965,123 A | 10/1990 | Sawan et al. | 428/314.4 |
| 4,978,486 A | 12/1990 | Ito et al. | 264/41 |
| 4,980,227 A | 12/1990 | Sekiguchi et al. | 428/241 |
| 5,006,394 A | 4/1991 | Baird | 428/138 |
| 5,008,296 A | 4/1991 | Antoon, Jr. et al. | 521/91 |
| 5,011,698 A | 4/1991 | Antoon, Jr. et al. | 426/395 |
| 5,019,073 A | 5/1991 | Roessler et al. | 604/391 |
| 5,026,591 A | 6/1991 | Henn et al. | 428/198 |
| 5,026,592 A | 6/1991 | Janocha et al. | 428/204 |
| 5,032,450 A | 7/1991 | Rechlicz et al. | 428/196 |
| 5,036,551 A | 8/1991 | Dailey et al. | 2/167 |
| 5,055,338 A | 10/1991 | Sheth et al. | 428/155 |
| 5,073,316 A | 12/1991 | Bizen et al. | 264/22 |
| 5,091,236 A | 2/1992 | Keller et al. | 428/213 |
| 5,110,670 A | 5/1992 | Janocha et al. | 428/216 |
| 5,110,677 A | 5/1992 | Barmore et al. | 428/349 |
| 5,116,662 A * | 5/1992 | Morman | 428/198 |
| 5,120,594 A | 6/1992 | Mrozinski | 428/195 |
| 5,126,197 A | 6/1992 | Schinkel et al. | 428/349 |

| | | | |
|---|---|---|---|
| 5,126,198 A | 6/1992 | Schinkel et al. | 428/349 |
| 5,143,679 A | 9/1992 | Weber et al. | 264/288.8 |
| 5,149,332 A | 9/1992 | Walton et al. | 604/358 |
| 5,164,258 A | 11/1992 | Shida et al. | 428/319.3 |
| 5,167,652 A | 12/1992 | Mueller | 604/385.1 |
| 5,169,712 A | 12/1992 | Tapp | 428/315.5 |
| 5,173,235 A | 12/1992 | Kamei et al. | 264/154 |
| 5,176,953 A | 1/1993 | Jacoby et al. | 428/315.5 |
| 5,204,179 A | 4/1993 | Baker et al. | 428/336 |
| 5,204,429 A | 4/1993 | Kaminsky et al. | 526/308 |
| 5,208,098 A | 5/1993 | Stover | 428/284 |
| 5,209,884 A | 5/1993 | Wood, Jr. | 264/41 |
| 5,212,009 A | 5/1993 | Peiffer et al. | 428/220 |
| 5,212,246 A | 5/1993 | Ogale | 525/240 |
| 5,218,036 A | 6/1993 | Kagawa et al. | 524/451 |
| 5,236,963 A | 8/1993 | Jacoby et al. | 521/92 |
| 5,238,623 A | 8/1993 | Mrozinski | 264/48 |
| 5,238,733 A * | 8/1993 | Joseph et al. | 428/284 |
| 5,241,031 A | 8/1993 | Mehta | 526/348.1 |
| 5,244,716 A | 9/1993 | Thornton et al. | 428/198 |
| 5,250,612 A | 10/1993 | Hazlitt et al. | 525/53 |
| 5,261,899 A | 11/1993 | Visscher et al. | 604/367 |
| 5,263,949 A | 11/1993 | Karami et al. | 604/383 |
| 5,272,236 A | 12/1993 | Lai et al. | 526/348.5 |
| 5,277,970 A | 1/1994 | Schuhmann et al. | 428/323 |
| 5,278,272 A | 1/1994 | Lai et al. | 526/348.5 |
| 5,284,540 A | 2/1994 | Roth et al. | 156/160 |
| 5,300,365 A | 4/1994 | Ogale | 428/461 |
| 5,317,035 A | 5/1994 | Jacoby et al. | 521/143 |
| 5,318,842 A | 6/1994 | Ogale | 428/349 |
| 5,324,576 A | 6/1994 | Reed et al. | 428/288 |
| 5,326,625 A | 7/1994 | Schuhmann et al. | 428/215 |
| 5,331,047 A | 7/1994 | Giacobbe | 525/88 |
| 5,336,552 A | 8/1994 | Strack et al. | 428/224 |
| 5,340,646 A | 8/1994 | Morita et al. | 428/307.3 |
| 5,342,884 A | 8/1994 | Tabor et al. | 525/64 |
| 5,372,882 A | 12/1994 | Peiffer et al. | 428/34.9 |
| 5,376,430 A | 12/1994 | Swenson et al. | 428/152 |
| 5,382,400 A | 1/1995 | Pike et al. | 264/168 |
| 5,382,461 A | 1/1995 | Wu | 428/86 |
| 5,385,972 A | 1/1995 | Yamamoto et al. | 524/579 |
| 5,397,635 A | 3/1995 | Wood, Jr. | 428/314.4 |
| 5,409,761 A | 4/1995 | Langley | 428/198 |
| 5,422,172 A | 6/1995 | Wu | 428/230 |
| 5,445,862 A | 8/1995 | Kaneko et al. | 428/148 |
| 5,453,318 A | 9/1995 | Giacobbe | 428/286 |
| 5,456,979 A | 10/1995 | Schirmer | 428/336 |
| 5,460,884 A | 10/1995 | Kobylivker et al. | 428/373 |
| 5,470,639 A | 11/1995 | Gessner et al. | 428/152 |
| 5,472,775 A | 12/1995 | Obijeski et al. | 428/220 |
| 5,482,770 A | 1/1996 | Bekele | 428/339 |
| 5,527,302 A | 6/1996 | Endres et al. | 604/385.1 |
| 5,539,124 A | 7/1996 | Etherton et al. | 548/402 |
| 5,554,775 A | 9/1996 | Krishnamurti et al. | 556/7 |
| 5,571,619 A | 11/1996 | McAlpin et al. | 428/364 |
| 5,582,923 A | 12/1996 | Kale et al. | 428/523 |
| 5,597,194 A | 1/1997 | Daugherty et al. | 296/39.2 |
| 5,605,735 A | 2/1997 | Zehner et al. | 428/100 |
| 5,616,420 A | 4/1997 | Yamaoka et al. | 428/515 |
| 5,624,991 A | 4/1997 | Harada et al. | 524/451 |
| 5,635,262 A | 6/1997 | Best et al. | 428/36.92 |
| 5,635,290 A | 6/1997 | Stopper et al. | 428/198 |
| 5,695,868 A | 12/1997 | McCormack | |
| 5,705,565 A * | 1/1998 | Hughes et al. | 525/65 |
| 5,804,011 A | 9/1998 | Dutta et al. | 156/160 |
| 5,847,053 A | 12/1998 | Chum et al. | 525/240 |
| 5,855,999 A * | 1/1999 | McCormack | 428/283 |
| 5,865,825 A * | 2/1999 | Schlinz | 604/385.2 |
| 5,885,707 A | 3/1999 | Kaschel et al. | 428/349 |

FOREIGN PATENT DOCUMENTS

| | | |
|---|---|---|
| EP | 0 221 726 | 5/1987 |
| EP | 0 247 897 | 12/1987 |
| EP | 0 259 128 | 3/1988 |
| EP | 0 265 128 | 5/1988 |
| EP | 0 329 377 | 8/1989 |
| EP | 0 330 019 | 8/1989 |
| EP | 0 347 745 | 12/1989 |
| EP | 0 395 204 | 10/1990 |
| EP | 0 434 115 | 6/1991 |
| EP | 0 456 044 | 11/1991 |
| EP | 0 233 704 | 7/1992 |
| EP | 0 505 027 | 9/1992 |
| EP | 0 546 837 | 6/1993 |
| EP | 0 380 353 | 9/1994 |
| EP | 0691203 | 1/1996 |
| EP | 0 712 892 | 5/1996 |
| EP | 0227481 | 7/1997 |
| GB | 1 452 424 | 10/1976 |
| GB | 1 453 649 | 10/1976 |
| GB | 1 557 920 | 12/1979 |
| GB | 2 223 446 | 4/1990 |
| GB | 2 267 459 | 12/1993 |
| JP | 4 227 260 | 8/1992 |
| WO | 90/03464 | 4/1990 |
| WO | 95/27005 | 10/1995 |
| WO | 96/19346 A | 6/1996 |
| WO | 97/04955 | 2/1997 |
| WO | 97/26297 | 7/1997 |
| WO | 98/02609 A | 1/1998 |
| WO | 98/02610 A | 1/1998 |
| WO | 98/04397 | 2/1998 |
| WO | 98/05501 | 2/1998 |
| WO | 98/29246 | 7/1998 |
| WO | 98/29479 | 7/1998 |
| WO | 98/29481 | 7/1998 |

OTHER PUBLICATIONS

Japanese Abstract 01–146733, Jun. 8, 1989.
Japanese Abstract 01–271240, Oct. 30, 1989.
Japanese Abstract 05–230251A, Feb. 19, 1992.
Japanese Abstract 08–64194, Mar. 8, 1996.
NRL Report 4364, "Manufacture of Superfine Organic Fibers" by V.A. Wente, E.L. Boone and C.D. Fluharty.
NRL Report 5265, "An Improved Device for the Formation of Superfine, Thermoplastic Fibers" by K. D. Lawrence, R.T. Lukas.
"New LLDPEs Offer Combined Properties, Processing Edge", Plastics World Apr. 1997, p. 8.
"Don't Say 'Metallocene,' Say 'Single–Site'", by Jan H. Schut, Plastics World, Apr. 1997, p. 27–32.
"Here's the Latest Score on Single Site Catalysts", by Jan H. Schut, Plastics World, Apr. 1997, pp. 41–46.
Japanese Abstract 03–198724A.
Japanese Abstract 02–162–008A.

* cited by examiner

STABLE BREATHABLE ELASTIC GARMENTS

This application claims priority from U.S. Provisional Application No. 60/059,001 filed on Sep. 17, 1997, the entire content of which is incorporated herein by reference.

FIELD OF THE INVENTION

The present invention relates to conformable garments and personal care products. More particularly, the present invention relates to barrier fabrics for disposable garments and personal care products.

BACKGROUND OF THE INVENTION

Film laminates have become an important article of commerce, finding a wide variety of applications including use within various articles; for example, as outer covers for personal care products such as diapers, training pants, incontinence garments, feminine hygiene products and the like. In addition, film laminates have found use in various other bodily articles such as garments, surgical gowns, protective workwear, wound dressings, bandages and the like. The films can provide the desired barrier properties to the article while other materials laminated thereto can provide additional desired characteristics such as abrasion resistance and/or good hand. In addition, in order to increase comfort of the wearer, film laminates are desirably "breathable" in the sense that the laminates act as a barrier to liquids but allow water vapor and air to pass therethrough. In addition, by achieving and maintaining high breathability it is possible to provide an article that is more comfortable to wear since the migration of water vapor through the fabric helps reduce and/or limit discomfort from excess moisture trapped against the skin. Thus, such an article can potentially contribute to an overall improved skin wellness.

While a variety of film laminates are known in the art, one particularly useful laminate uses a breathable barrier comprising a stretched filled microporous film. Such films are typically filled with particles or other matter and then crushed or stretched to form a fine pore network throughout the film. The pores result from the separation of the polymer from the filler particles. The film pore network allows gas and water vapor to pass through the film while acting as a barrier to liquids and particulate matter. The amount of filler within the film and the degree of stretching is controlled so as to create a network of micropores of a size and/or frequency to impart the desired level of breathability to the fabric. An exemplary stretched filled-film is described in commonly assigned WO Patent Application 95/16562 to McCormack which discloses a filled-film comprising a predominantly linear polyolefin polymer, a bonding agent and about 30 to 80% by weight calcium carbonate, wherein the filled-film can be stretched to impart breathability to the film. The stretched film may then be laminated to a nonwoven web to create a laminate that takes advantage of the strength and integrity of the nonwoven web and the barrier properties of the stretched film.

In addition to breathability of the film laminate, the ability of the garment to exhibit elastic properties allows the garment to provide better body conformance. However, providing a low cost laminate that achieves the desired conformance and breathability is problematic, particularly with stretched filled-films. In order to achieve good body conformance, the polymer composition of the film desirably has good stretch and recovery properties and yet must also be capable of allowing formation and retention of pores upon processing. Furthermore, the breathable film laminate must be sufficiently stable so as to maintain the desired characteristics while in use (e.g. at about 37° C. or body temperature) as well as over time and shelf-aging. For example, such garments will often be exposed to temperatures up to about 54° C. or more in transport, storage, or during additional processing. Often exposure to such temperatures can cause shrinkage of the film which results in buckling and/or puckering of the fabric. This results in a product that is less aesthetically pleasing and gives the impression of a product of lesser quality. Further, the buckling may result in delamination which, in addition to being aesthetically undesirable, can increase the risk that the film will be ripped or torn. Moreover, it has been found that these conditions can also decrease the breathability and reduce the stretch-recovery of the fabric.

Thus, there exists a need for a film and laminate thereof which is capable of providing good breathability (i.e. WVTR) and body conformance at body temperature. Further, there exists a need for such a film and laminates thereof that are sufficiently heat stable to maintain the desired properties when subjected to the conditions commonly experienced in further processing, storage and/or transportation. Further, there likewise exists a need for a low cost film and film laminate that provides good breathability and body conformance that has overall improved aesthetics and that does not suffer from shrinkage and/or excessive hysteresis.

SUMMARY OF THE INVENTION

The aforesaid needs are fulfilled and the problems experienced by those skilled in the art overcome by the microporous film of the present invention which comprises a thermoplastic polymer blend of a first polyethylene polymer having a density below 0.89 g/cm$^3$ and a second polyethylene polymer having a density above about 0.90 g/cm$^3$. The first polyethylene polymer can comprise between 25% and 75% by weight of the thermoplastic polymer component of the film. Additionally, the microporous film can include a filler comprising at least 35% by weight of total weight of the film. The filled-film can be oriented to create a microporous film having voids adjacent to the filler wherein the film has a WVTR of at least 300 g/m$^2$/24 hours at 37° C. and less than 15% heat shrinkage at 37° C. The resulting microporous film of the present invention exhibits a combination of good body conformance and breathability at temperatures experienced in use and/or transport. Further, the first polyethylene polymer can have a density between about 0.89 g/cm$^3$ and about 0.86 g/cm$^3$ and the second polyethylene polymer a density between about 0.90 g/cm$^3$ and about 0.92 g/cm$^3$. Desirably, each of the first and second polyethylene polymers within the thermoplastic polymer blend can comprise between about 35% and about 65% by weight of the thermoplastic polymer component and, still more desirably, each of the first and second polyethylene polymers comprises about 50% by weight of the thermoplastic polymer component.

In a further aspect of the invention, the microporous film of the present invention can be laminated to a fibrous layer wherein the film laminate has a shrinkage less than 5% at 54° C. and even more desirably has a shrinkage of less than about 1% at 54° C. The fibrous layer can comprise a nonwoven web such as, for example, an extensible nonwoven web. Film nonwoven laminates of the present invention can be used as a barrier layer in bodily articles such as, for example, in diapers, adult incontinence garments, protective apparel and the like. Additionally, and in still a further aspect of the present invention, the breathable microporous films and/or film laminates of the present invention can comprise a component of an absorbent bodily article. As one example, an absorbent bodily article can comprise a liquid pervious liner; an absorbent core; and a microporous film or film laminate of the present invention wherein the absorbent core is positioned between the liquid pervious liner and microporous film or film laminate.

DEFINITIONS

Figure 1:
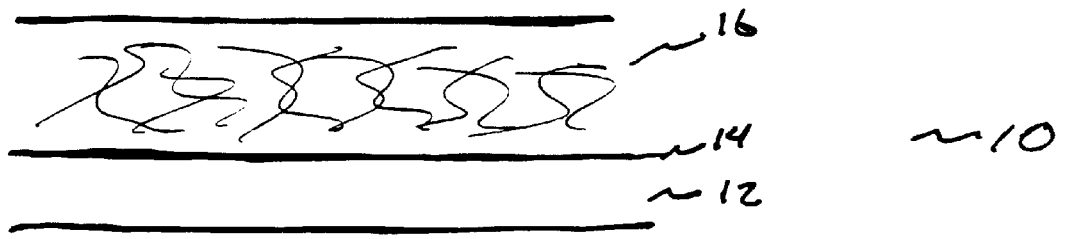
FIG. 1 is a cross-sectional view of a film laminate of the present invention.

As used herein and in the claims, the term "comprising" is inclusive or open-eneded and does not exclude additional unrecited elements, compositional components, or method steps. As used herein the term "nonwoven" fabric or web means a web having a structure of individual fibers or threads which are interlaid, but not in an identifiable manner as in a knitted fabric. Nonwoven fabrics or webs have been formed by many processes such as for example, meltblowing processes, spunbonding processes, hydroentangling, air-laid and bonded carded web processes.

As used herein the term "extensible" means elongatable or stretchable in at least one direction.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. Spunbond fibers are generally not tacky when they are deposited onto a collecting surface and are generally continuous. Spunbond fibers are often about 10 microns or greater in diameter. However, fine fiber spunbond webs (having an average fiber diameter less than about 10 microns) may be achieved by various methods including, but not limited to, those described in commonly assigned U.S. patent applications Ser No. 08/756,426 filed Nov. 26, 1996 to Marmon et al. and application Ser. No. 08/565,261 filed Nov. 30, 1995 to Pike et al. (now U.S. Pat. No. 5,759,926).

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. and U.S. Pat. No. 5,271,883 to Timmons et al. Meltblown fibers may be continuous or discontinuous, are generally smaller than 10 microns in average diameter, and are generally tacky when deposited onto a collecting surface.

As used herein "multilayer nonwoven laminate" means a laminate of two or more nonwoven layers such as, for example, wherein some of the layers are spunbond and some meltblown such as a spunbond/meltblown/spunbond (SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spacial configurations of the molecule. These configurations include, but are not limited to isotactic, syndiotactic and random symmetries.

As used herein, the term "machine direction" or MD means the length of a fabric in the direction in which it is produced. The term "cross machine direction" or CD means the width of fabric, i.e. a direction generally perpendicular to the MD.

As used herein, "ultrasonic bonding" means a process performed, for example, by passing the fabric between a sonic horn and anvil roll as illustrated in U.S. Pat. No. 4,374,888 to Bornslaeger.

Figure 3:
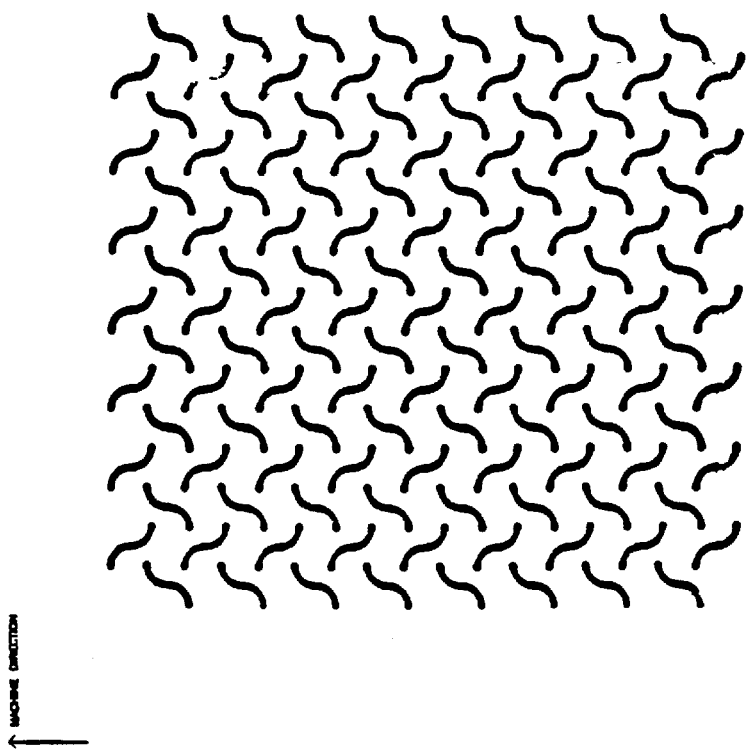
FIG. 3 is a schematic view of a bonding pattern suitable for use with the present invention.
Figure 4:
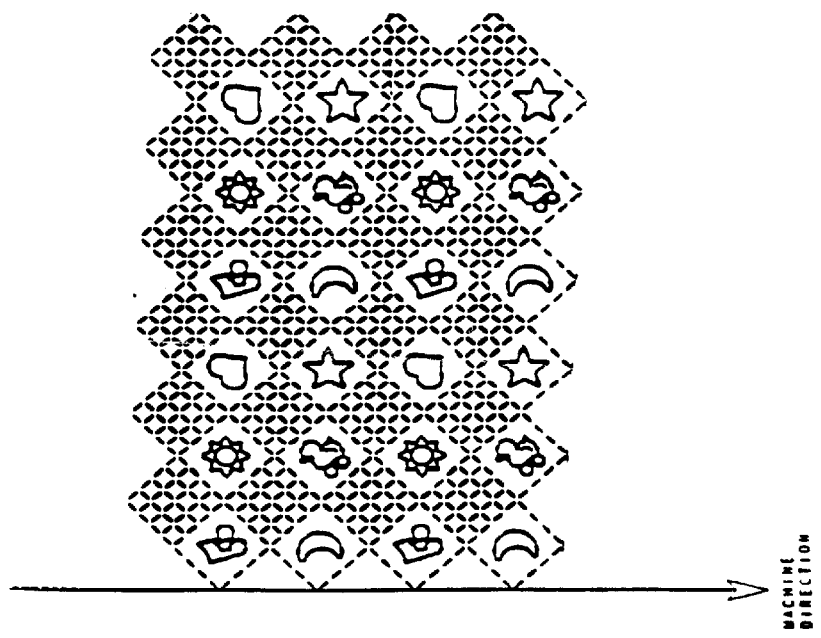
FIG. 4 is a schematic view of a bonding pattern suitable for use with the present invention.

As used herein "point bonding" means bonding one or more layers of fabric at a plurality of discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a point bond pattern is the Hansen Pennings or "H&P" pattern with about a 30% bond area when new and with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5% when new. Another typical point bonding pattern is the expanded Hansen Pennings or "EHP" bond pattern which produces a 15% bond area when new with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15% when new. Yet another common pattern is the C-Star pattern which has, when new, a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 15% bond area. A further pattern is the "s-weave" pattern having about a 17% bond area when new and as generally shown with reference to FIG. 3 and a baby objects pattern having about a 12% bond area when new and as generally shown in FIG. 4. Typically, the percent bonding area is less than about 50% and more desirably varies from around 10% to around 30% of the area of the fabric laminate web.

As used herein "elastic" or "elastomeric" refers to material which, upon application of a biasing force, is extensible or elongatable in at least one direction and returns approximately to its original dimensions after the force is removed. For example, an elongated material having a biased length which is at least 50% greater than its relaxed unbiased length, and which will recover to within at least 50% of its elongation upon release of the elongating force. A hypothetical example would be a one (1) inch sample of a material which is elongatable to at least 1.50 inches and which, upon release of the biasing force, will recover to a length of not more than 1.25 inches.

As used herein, the term "inelastic" or "nonelastic" refers to any material which does not fall within the definition of "elastic" above.

As used herein, the term "barrier" means a film, laminate or other fabric which is relatively impermeable to the transmission of liquids and which has a hydrohead of at least 50 mbar. Hydrohead as used herein refers to a measure of the liquid barrier properties of a fabric and is discussed in more detail herein below. However, it should be noted that in many applications of barrier fabrics, including those of the present invention, it may be desirable that they have a hydrohead value greater than about 80 mbar, 150 mbar or even 300 mbar.

As used herein, the term "breathable" refers to a material which is permeable to water vapor having a minimum WVTR (water vapor transmission rate) of about 300 g/m$^{2124}$ hours. The WVTR of a fabric, in one aspect, gives an indication of how comfortable a fabric would be to wear. WVTR is measured as indicated below and the results are reported in grams/square meter/24 hours. However, often applications of breathable barriers desirably have higher WVTRs and breathable barriers of the present invention can have WVTRs exceeding about 500 g/m$^2$/24 hours, 800 g/m$^{2124}$ hours, 1500 g/m$^{2124}$ hours or even exceeding 3000 g/m$^2$/24 hours.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc.

As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers are usually different from each other and are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea" type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers are also taught in U.S. Pat. No. 5,382,400 to Pike et al. and may be used to produce crimp in the fibers by using the differential crystallization rates of the two (or more) polymers. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "blend" means a mixture of two or more polymers while the term "alloy" means a sub-class of blends wherein the components are immiscible but have been compatibilized.

As used herein the term "biconstituent fibers" or "multiconstituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, ISBN 0-306-30831-2, at pages 273 through 277.

As used herein, the term "scrim" means a lightweight fabric used as a backing material. Scrims are often used as the base fabric for coated or laminated products.

As used herein, the term "garment" means any type of non-medically oriented apparel which may be worn. This includes industrial work wear and coveralls, undergarments, pants, shirts, jackets, gloves, socks, and the like.

As used herein, the term "infection control product" means medically oriented items such as surgical gowns, face masks, head coverings like bouffant caps, surgical caps and hoods, bandages, dressings, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein, the term "personal care product" means diapers, training pants, absorbent underpants, adult incontinence products, and feminine hygiene products.

As used herein, the term "bodily article" means any article which may be worn by a person and include, but are not limited to, personal care products, garments, infection control products and the like.

As used herein and in the claims, the term "comprising" is inclusive or open-ended and does not exclude additional unrecited elements, compositional components, or method steps.

DETAILED DESCRIPTION OF THE INVENTION

Figure 2:
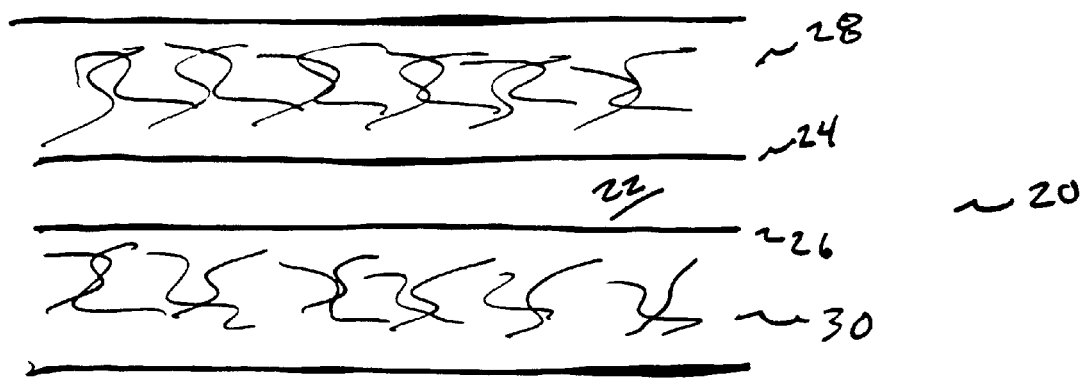
FIG. 2 is a cross-sectional view of a film laminate of the present invention.

In reference to FIG. 1, a breathable filled-film 12 of the present invention is particularly well suited for use in a film laminate 10. The breathable filled-film 12 has a first side 14 which can be bonded to a fibrous layer and/or support fabric 16, desirably an extensible cloth-like fabric. The laminate can comprise a bodily article or a component of such an article. In a further aspect and in reference to FIG. 2, the breathable filled-film 22 can be bonded on its first side 24 to a first fibrous layer 28 and on its second side 26 to a second fibrous fabric 30. The first and second fibrous layer and/or support fabrics can be selected to provide the desired support, elasticity or other properties as desired and need not comprise identical fabrics.

The breathable filled-film comprises at least two components including a polymer blend and filler. The breathable film desirably comprises a filled barrier film having a WVTR of at least 300 g/m$^2$/24 hours, desirably in excess of 500 g/m$^2$/24 hours, 800 g/m$^2$/24 hours, 1500 g/m$^2$/24 hours or even 2500 g/m$^2$/24 hours. In addition, the breathable filled-film desirably has a basis weight less than about 60 g/m$^2$ and even more desirably between about 10 and 35 g/m$^2$ and still more desirably between about 15 g/m$^2$ and 25 g/m$^2$. The breathable filled-film 12 can be formed by any one of various methods known in the art. Desirably first breathable film comprises a microporous film such as a stretched filled-film comprising a stable thermoplastic polymer blend and filler. These (and other) components can be mixed together, heated and then extruded into a film. The filled film may be made by any one of a variety of film forming processes known in the art such as, for example, by using either cast or blown film equipment. The breathable filled-film can comprise mono-layer or multi-layer films. As an example, the breathable film can comprise a breathable base film and a thin breathable outer layer which are simultaneously made such as, for example, formed by co-extrusion. As an example, methods of forming multilayer films are disclosed in U.S. Pat. No. 4,522,203; U.S. Pat. No. 4,494,629; U.S. Pat. No. 4,734,324 and WO 96/19346 filed Jun. 27, 1996 to McCormack et al.; and U.S. Application (Express Mail No. RB879662575US) Ser. No. 08/882,712 and filed Sep. 15, 1997 to Haffner et al., the entire contents of which are incorporated herein by reference. Processes for producing thermally bondable breathable stretched filled-films are also disclosed in U.S. Pat. No. 5,695,868 and WO 95/16562 filed Jun. 22, 1995 to McCormack, the entire contents of which are incorporated herein by reference.

In a preferred embodiment the breathable filled-film, or base layer of a multi-layer film, is a film made from a thermoplastic polymer blend which was stretched in at least one direction, thereby reducing the film gauge or thickness and forming a micropore network. The stable thermoplastic polymer blend comprises a low density ethylene polymer and a higher density more crystalline ethylene polymer component. The low density ethylene polymer desirably comprises an ethylene polymer having a density of less than 0.89 g/cm$^3$, desirably having a density between about 0.86 g/cm$^3$ and 0.89 g/cm$^3$ and even more desirably having a density between about 0.863 g/cm$^3$ and about 0.88 g/cm$^3$. The low density ethylene polymer component is desirably blended with a more crystalline ethylene polymer having a density between about 0.90 g/cm$^3$ and about 0.92 g/cm$^3$ and more desirably having a density between about 0.90 g/cm$^3$ and about 0.917 g/cm$^3$. In a particularly preferred embodiment, the ethylene polymer has a density of about 0.87 g/cm$^3$ and the higher density ethylene polymer has a density of about 0.91 g/cm$^3$. The ratio (by weight % of the polymeric component) of low density elastomeric ethylene to the more crystalline or higher density ethylene polymer is from 75/25 to 25/75 and desirably from 70/30 to 30/70. Still more desirably the low density elastomeric ethylene to the higher density ethylene blended in a ratio of from about 60/40 to about 40/60 and even more desirably about 50/50.

The low density ethylene can be a plastomer or an elastomer. In one embodiment of the present invention, the low density ethylene polymer or polyethylene polymer can comprise substantially linear polymers wherein the ethylene monomers are polymerized with an alpha-olefin such that the resulting polymer composition has a narrow molecular weight distribution ($\overline{M}_w/\overline{M}_n$) of about 2, homogeneous branching and controlled long chain branching. Suitable alpha-olefins include, but are not limited to, 1-octene, 1-butene, 1-hexene and 4-methyl-pentene. Exemplary polymers include those known in the art as "metallocene", "single-site" or "constrained geometry" catalyzed polymers such as those described in U.S. Pat. No. 5,472,775 to Obijeski et al. and assigned to the Dow Chemical company, the entire contents of which are incorporated herein by reference. The metallocene process generally uses a metallocene catalyst which is activated, i.e. ionized, by a co-catalyst. Examples of metallocene catalysts include bis (n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow. However, numerous other metallocene, single-site and/or similar catalyst systems are known in the art; see for example, U.S. Pat. No. 5,539,124 to Etherton et al.; U.S. Pat. No. 5,554,775 to Krishnamurti et al.; U.S. Pat. No. 5,451,450 to Erderly et al. and *The Encyclopedia of Chemical Technology*, Kirk-Othemer, Fourth Edition, vol. 17, Olefinic Polymers, pp. 765–767 (John Wiley & Sons 1996); the entire content of the aforesaid patents are incorporated herein by reference.

Regarding metallocene based plastomers or elastomeric polymers, U.S. Pat. No. 5,204,429 to Kaminsky et al. describes a process for producing elastic copolymers from cycloolefins and linear olefins using a catalyst which is a stereorigid chiral metallocene transition metal compound and an aluminoxane. The reaction may also occur in the gas phase using the monomers to be polymerized as the solvent. U.S. Pat. Nos. 5,278,272 and 5,272,236, both to Lai et al., assigned to Dow Chemical and entitled "Elastic Substantially Linear Olefin Polymers" describe polymers having particular elastic properties, the entire contents of which are incorporated herein by reference. Suitable low density ethylene elastomers are commercially available from Dow Chemical Company of Midland, Mich. under the trade name AFFINITY™, including AFFINITY™ EG8200 (5 MI), XU 58200.02 (30 MI), XU 58380.00 (10 MI) and from Exxon Chemical Co. of Houston, Tex. a under the trade name EXACT™, including EXACT 4049 (4.5 MI, 0.873 g/cm$^3$); 4011 (2.2 MI, 0.888 g/cm$^3$); 4041 (3 MI, 0.878 g/cm$^3$; 4006 (10 MI, 0.88 g/cm$^3$).

The higher density, more crystalline ethylene polymer can also be produced by catalysts similar to those described above, e.g. metallocene, single site or constrained geometry catalysts. Additionally, higher density ethylene polymers can be made by more traditional catalyst systems such as Ziegler-Natta catalysts. Desirably these polymers have a density between about 0.900 g/cm$^3$ and about 0.920 g/cm$^3$. Suitable ethylene polymers include ethylene polymers commonly known as "linear low density polyethylene" (LLDPE) and "high density polyethylene" (HDPE). A variety of these ethylene polymers are commercially available including as examples, those under the trade designation AFFINITY™, ELITE™ or ASPUN™ available from Dow Chemical Company and EXCEED™ available from Exxon Chemical Co.

Additional film forming polymers which may be suitable for use with the present invention, in combination with the ethylene polymer blend, include ethylene-propylene copolymers, ethylene vinyl acetate (EVA), ethylene ethyl acrylate (EEA), ethylene acrylic acid (EAA), ethylene methyl acrylate (EMA), ethylene normal butyl acrylate (EnBA), polyurethane (PU), polyether esters, polyether amides, EPDM rubbers and the like.

In addition to the thermoplastic polymer blend, the breathable filled-film also includes a filler to impart breathability to the film. As used herein a "filler" is meant to include particulates and/or other forms of materials which can be added to the film polymer extrusion blend which will not chemically interfere with or adversely affect the extruded film and further which are capable of being uniformly dispersed throughout the film. Generally the fillers will be in particulate form with average particle sizes in the range of about 0.1 to about 10 microns, desirably from about 0.1 to about 4 microns. As used herein the term "particle size" describes the largest dimension or length of the filler. Both organic and inorganic fillers are contemplated for use with the present invention provided they do not interfere with the film forming process and/or subsequent laminating processes. Examples of fillers include calcium carbonate ($CaCO_3$), various clays, silica ($SiO_2$), alumina, barium sulfate, sodium carbonate, talc, magnesium sulfate, titanium dioxide, zeolites, aluminum sulfate, cellulose-type powders, diatomaceous earth, gypsum, magnesium sulfate, magnesium carbonate, barium carbonate, leaolin, mica, carbon, calcium oxide, magnesium oxide, aluminum hydroxide, pulp powder, wood powder, cellulose derivatives, polymeric particles, chitin and chitin derivatives. The filler particles may optionally be coated with a fatty acid, such as stearic acid or behenic acid, and/or other material in order to facilitate the free flow of the particles (in bulk) and their ease of dispersion into the polymer. The filled-film will usually contain at least 35% filler based upon the total weight of the film layer, more desirably from about 50% to about 70% by weight filler. Due to the nature of the polymer blend, roll blocking can occur when less than about 50% filler is utilized. Thus, where lower levels of filler are used additional processing aids and/or modification of the processing may be necessary to prevent the same.

In addition, the breathable filled-film may optionally include one or more stabilizers. Desirably the filled-film includes an anti-oxidant such as, for example, a hindered phenol stabilizer. Commercially available anti-oxidants include, but are not limited to, IRGANOX™ E 17 (α-tocopherol) and IRGANOX™ 1076 (octodecyl 3,5-ditert-butyl-4-hydroxyhydrocinnamate) which are available from Ciba Specialty Chemicals of Terrytown, N.Y. In addition, other stabilizers or additives which are compatible with the film forming process, stretching and any subsequent lamination steps may also be employed with the present invention. For example, additional additives may be added to impart desired characteristics to the film such as, for example, melt stabilizers, processing stabilizers, heat stabilizers, light stabilizers, heat aging stabilizers and other additives known to those skilled in the art. Generally, phosphite stabilizers (i.e. IRGAFOS 168 available from Ciba Specialty Chemicals of Terrytown, N.Y. and DOVERPHOS available from Dover Chemical Corp. of Dover, Ohio) are good melt stabilizers whereas hindered amine stabilizers (i.e. CHIMASSORB 944 and 119 available from Ciba Specialty Chemicals of Terrytown, N.Y.) are good heat and light stabilizers. Packages of one or more of the above stabilizers are commercially available such as B900 available from Ciba Specialty Chemicals. Desirably about 100 to 2000 ppm of the stabilizers is added to the base polymer(s) prior to extrusion. (Parts per million is in reference to the entire weight of the filled-film.)

In a preferred embodiment of the invention the filled-film is laminated to an outer fibrous layer. Suitable materials include nonwoven fabrics, multi-layered nonwoven fabrics, scrims, woven fabrics and other like materials. In order to achieve a laminate with improved body conformance, the fibrous layer is desirably an extensible fabric and even more desirably an elastic fabric. For example, tensioning a nonwoven fabric in the MD causes the fabric to "neck" or narrow in the CD and give the necked fabric CD stretchability. Examples of additional suitable extensible and/or elastic fabrics include, but are not limited to, those described in U.S. Pat. No. 4,443,513 to Meitner et al.; U.S. Pat. No. 5,116,662 to Morman et al.; U.S. Pat. No. 4,965,122 to Morman et al.; U.S. Pat. No. 5,336,545 to Morman et al.; U.S. Pat. No. 4,720,415 to Vander Wielen et al.; U.S. Pat. No. 4,789,699 to Kieffer et al.; U.S. Pat. No. 5,332,613 to Taylor et al.; U.S. Pat. No. 5,288,791 to Collier et al.; U.S. Pat. No. 4,663,220 to Wisneski et al.; U.S. Pat. No. 5,540,976 to Shawver et al.; European Application No. 0,712,892 A1 to Djiaw et al.; U.S. application Ser. No. 08/603,961 to Shawver et al. and U.S. application Ser. No. 08/674,365 to Levy et al., the entire content of the aforesaid patents are incorporated herein by reference. Nonwoven fabrics desirably have a basis weight between about 10 g/m$^2$ and about 70 g/m$^2$ and even more desirably between about 15 g/m$^2$ and about 34 g/m$^2$. As a particular example, a 17 g/m$^2$ (0.5 ounces per square yard) web of propylene spunbond fibers can be necked a desired amount and thereafter laminated to a breathable stretched filled-film.

The outer support layer can be laminated to the breathable filled-film by one or more means known in the art. The support layer and filled-film can be bonded, e.g. point bonded, by imparting sufficient energy to the film and/or fibrous fabric to cause the materials to soften and/or flow such as, for example, by applying thermal, ultrasonic, microwave and/or compressive force or energy. Bonding agents or tackifiers may be added to the film to improve adhesion of the layers. In a further aspect of the invention, the filled-film and fibrous layer can be adhesively laminated to one another. In order to achieve improved drape the adhesive is desirably pattern applied to one of the fabrics or applied only to the outer fibrous layer. By applying the adhesive to the outer fibrous layer, such as a nonwoven fabric, the adhesive will generally only overlie the film at fiber contact points and thus provide a laminate with improved drape and/or breathability. Examples of suitable adhesives include, but are not limited to, REXTAC™ 2730 from Huntsman Corporation of Salt Lake City, Utah; H2525A which is a styrene block copolymer adhesive available from Findley Adhesives, Inc. of Wauwatusa, Wis.; and 34-5610 which is a styrene block copolymer adhesive available from National Starch, Starch and Chemical Co. of Bridgewater, N.J. Commercially available amorphous polyalphaolefins (APAO) used in hot melt adhesives suitable for use with the present invention include, but are not limited to, REXTAC™ ethylene-propylene APAO E-4 and E-5 and butylene-propylene BM-4 and BH-5 from Huntsman Corporation of Salt Lake City, Utah, and VESTOPLAST™ 792 from Hüls AG of Marl, Germany. Amorphous polyalphaolefins can be synthesized on a Ziegler-Natta supported catalyst and an alkyl aluminum co-catalyst and the olefin, such as propylene, is polymerized in combination with varied amounts of ethylene, 1-butene, 1-hexane or other materials to produce a predominantly atactic hydrocarbon chain. In a preferred embodiment, from about 1 $g/m^2$ to about 10 $g/m^2$ of adhesive is applied to a fibrous support fabric prior to superposing the support layer and filled-film. Additional bonding aids or tackifiers, such as described in WO 95/16562 can also be used.

Figure 5:
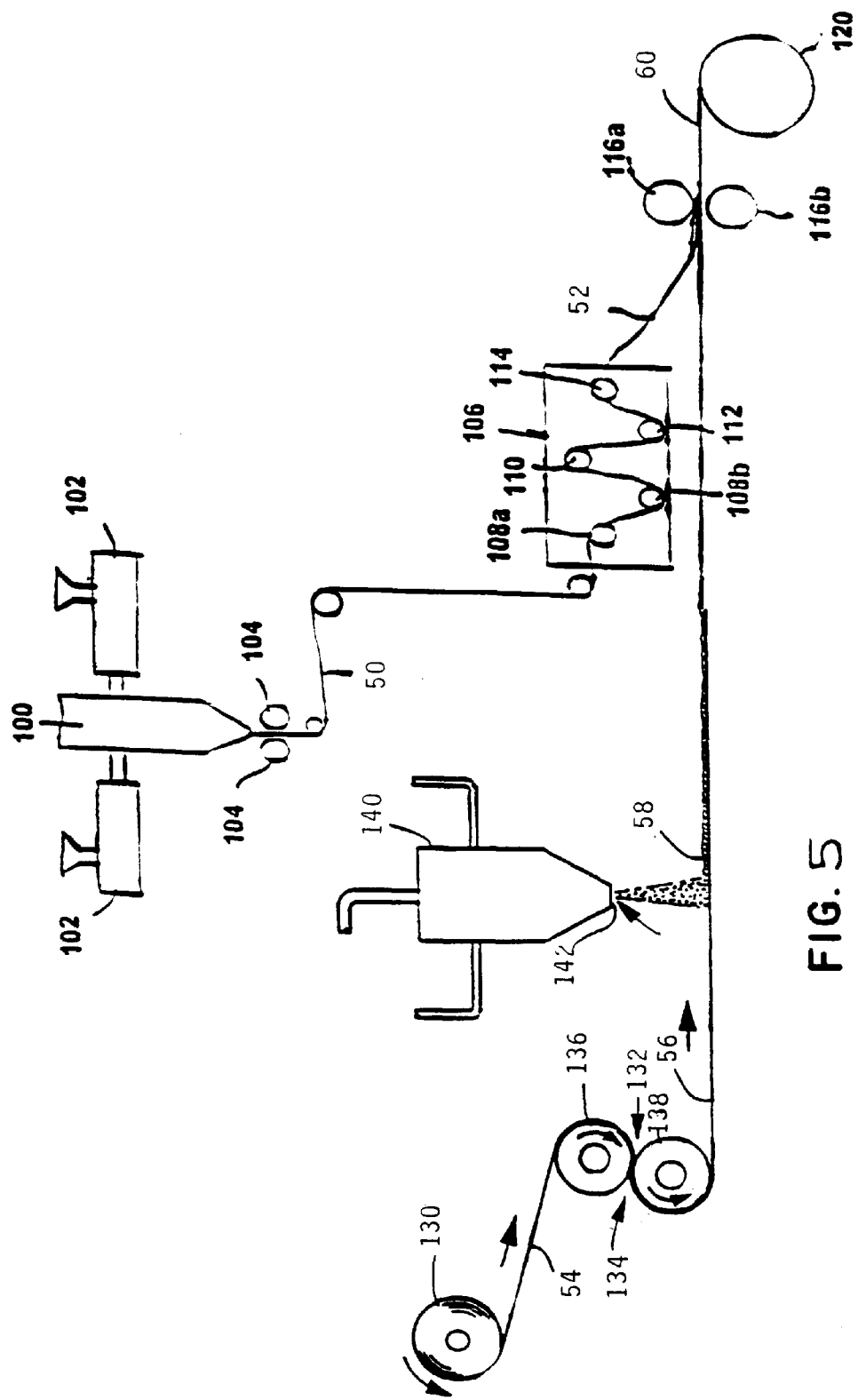
FIG. 5 is a schematic diagram of a process line for making film laminates of the present invention.

In reference to FIG. 5, a schematic diagram of a process line for fabricating breathable barrier laminates of the present invention. Referring to FIG. 5, a filled-film can be formed from an extrusion film apparatus 100 such as a cast or blown film unit. Typically the apparatus 100 will include one or more polymer extruders 102. The unstretched filled film 50 is extruded into a pair of nip or chill rollers 104 one of which may be patterned so as to impart an embossed pattern to the newly formed filled-film 50. This may be desired in some applications in order to reduce the gloss of the film and give it a matte finish. Although the basis weight of the unstretched filled-film will vary with respect to the stretch ratio, the desired final film basis weight and other parameters, desirably the basis weight of the unstretched filled-film will vary from about 50 $g/m^2$ to about 120 $g/m^2$.

From the extrusion film apparatus 100 the unstretched film 50 is directed to a film stretching unit 106 such as a machine direction orienter which is a commercially available device from vendors such as the Marshall and Williams Company of Providence, R.I. Such an apparatus 106 has a plurality of preheat and stretching rollers which stretch and thin the unstretched film 50 in the machine direction (MD) of the film which is the direction of travel of the film 50 through the process. The film can be stretched in either single or multiple discrete stretching operations. Desirably the unstretched filled-film will be stretched from about 2 to about 6 times its original length. With regard to FIG. 5, heated rollers 108a and 108b may act as pre-heat rolls. Slow roll 110 travels at a circumferential speed slower than that of fast roll 112. The different speeds of the adjacent rollers act to stretch the filled-film 50. One or both of the slow roll 110 and fast roll 112 can be heated. After stretching, the film may be allowed to slightly retract and/or be further heated or annealed by one or more heated rollers, such as by heated anneal roll 114. After exiting the film stretching unit 106 the stretched film 52 desirably has a basis weight less than about 60 $\mu m^2$, and even more desirably having a basis weight between about 15 and about 35 $g/m^2$.

The stretched filled-film 52 can be attached to an extensible fibrous layer 56, such as a necked spunbonded web, to form a film/nonwoven laminate 60. Referring again to FIG. 5, a neckable material 54 is unwound from a supply roll 130. The neckable material 54 then travels in the direction indicated by the arrows associated therewith. The neckable material 54 then passes through nip 132 of S-roll arrangement 134, formed by stack of rollers 136 and 138, in a reverse S-wrap path as indicated by the arrows associated with stack rollers 136 and 138. Because the peripheral or circumferential speed of the rollers of the S-roll arrangement 134 is controlled to be slower than the peripheral linear speed of the calendar roll assembly 116, the neckable material 54 is tensioned so that it necks a desired amount. The necked material could alternately be necked off-line and unrolled in the tensioned, necked condition. The necked material 56 is maintained in the tensioned, necked condition as it passes under spray equipment 140 which sprays an adhesive 58 through die head 142 onto the necked material 56. Once the stretched filled-film 52 has been sufficiently thinned, the necked material 56 formed and adhesive 58 applied thereto, the layers can be brought together and the adhesive treated (if necessary, e.g. with heat) thereby forming a stable breathable laminate 60 with excellent body conformance. Optionally, the laminate may be further bonded or embossed using calendering rolls 116a, 116b. One and/or both of the calender rolls may be heated. The bonding rolls 116a, 116b are desirably heated and at least one of the rolls may be patterned to create a desired bond pattern with a prescribed bond surface area for the resultant laminate. Once the laminate 60 exits the bonding rolls 116a and 116b, it may be wound up into a winder roll 120. Alternatively, the laminate 60 may continue in-line for further processing and/or conversion.

The barrier laminates of the present invention may be used to either make or comprise a component of protective fabrics, infection control products, personal care products, garments and other articles that desirably have barrier properties and breathability. As specific examples thereof, the barrier laminates may be used as follows: as a back sheet or an outer cover in a diaper or adult incontinence garments such as described in U.S. Pat. No. 5,415,644 to Enloe and U.S. patent application Ser. No. 08/994,530 to Strack et al.; or as a barrier layer in surgical gowns and protective apparel such as described in U.S. Pat. No. 4,823,404 to Morrell et al.; U.S. Pat. No. 5,509,142 to Connell et al.; U.S. Pat. No. 5,487,189 to Bell and U.S. Pat. No. 5,492,753 to Levy et al.; the entire content of the aforesaid patents and applications are incorporated herein by reference.

Tests

Hydrohead: A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. The hydrohead data cited herein was obtained using a test method similar to the aforesaid Federal Test Standard except as modified and noted below. The hydrohead was determined using a hydrostatic head tester available from Marlo Enterprises, Inc. of Concord, N.C. The specimen is subjected to a standardized water pressure (as opposed to a column of water as in the Federal Test Standard) which is increased at a constant rate until leakage appears on the surface of the fabric in three separate areas. (Leakage at the edge, adjacent to the clamps is ignored.) Unsupported fabrics, such as a thin film, can be supported to prevent premature rupture of the specimen.

Melt Index: The melt index (MI) is a measure of the viscosity of a polymer at a given set of conditions. The MI is expressed as the mass of material which flows from a capillary of known dimensions under a specified load or shear rate for a measured period of time and is measured in grams/10 minutes at 190° C. and load of 2160 g according to ASTM test 1238-90b.

WVTR: The water vapor transmission rate (WVTR) for the sample materials was calculated in accordance with ASTM Standard E96-80. Circular samples measuring three inches in diameter were cut from each of the test materials and a control which was a piece of CELGARD® 2500 film from Hoechst Celanese Corporation of Sommerville, N.J. CELGARD® 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at about 100° F. (38° C.) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

$$\text{Test WVTR}=(\text{grams weight loss over 24 hours})\times 315.5 \ g/m^2/24 \ \text{hours} \quad (I)$$

The relative humidity within the oven was not specifically controlled.

Under the predetermined set conditions of about 100° F. (38° C.) and ambient relative humidity, the WVTR for the CELGARD® 2500 control has been defined to be 5000 grams per square meter for 24 hours. Accordingly, the control sample was run with each test and the preliminary test values were corrected to set conditions using Equation (II) below:

$$\text{WVTR}=(\text{Test WVTR/control WVTR})\times(5000 \ g/m^2/24 \ \text{hours}) \quad (II)$$

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape or some other suitable material in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position and the clamps move apart at the specified rate of extension to pull the laminate apart. The sample specimen is pulled apart at 180° of separation between the two layers and the peel strength reported as an average of peak load in grams. Measurement of the force is begun when 16 mm of the laminate has been pulled apart and continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Phila., PA 19154, may be used for this test. Results are reported as an average of three specimens and may be performed with the specimen in the cross direction (CD) or the machine direction (MD).

% Heat Shrinkage: A 12 inch×14 inch section of fabric is placed in an oven for approximately 4 minutes at a predetermined temperature (e.g. 37° C. or 54° C.). Prior to heating, the fabric is marked at set intervals in the direction of orientation. After heating the fabric is again measured, the decrease in distance between the marked intervals is measured to obtain the % of shrinkage.

Extension/Retraction (Six Cycle to 50% elongation test): A 3 inch by 6 inch sample is pulled to a target elongation of 50% at a rate of 20 in/min, and returned to the original distance of two inches for six cycles. At the top of the seventh cycle, the sample is held for 1 minute. The sample is then returned to the original grip distance and held for 1 minute. The sample is then pulled until a load of 10 g is detected. Immediate recovery, delayed recovery and percent set are calculated. Extension tension and retraction tension are calculated at 30% elongation on the first and second cycles, respectively. Testing is done on the Sintech 1/S or 2/S equipment utilizing TESTWORKS for Windows 3.02 software to record data.

$$\text{Hysteresis} = \frac{\text{Force of Extension-Force of Retraction}}{\text{Force of Extension}}$$

EXAMPLE 1

A 100 g/m² film was made by a standard blown film process and comprised 55% by weight calcium carbonate filler coated with stearic acid and about 45% by weight polymer. The polymer comprised a blend of 75% by weight of a low density polyethylene elastomer, AFFINITY EG8200 (0.87 g/cm³, 5 MI) available from Dow Chemical Co., and 25% by weight of a linear low density polyethylene AFFINITY PL 1845 (0.91 g/cm², 3.5 MI) available from Dow Chemical Co. The film was then stretched in the machine direction 5.3 times its original length using a machine direction orienter available from Marshall and Williams Co. The slow roll was at ambient temperature and had a speed of about 42 feet per minute (fpm), the fast roll was at 130° F. and had a speed of about 217 fpm. The annealing rolls were at 130° F. and ambient temperature, the speed of the respective anneal rolls were 204 fpm and 135 fpm. The stretched film was allowed to retract over the anneal rolls, resulting in a breathable microporous film having final stretch ratio of 3.3 times its original length and a basis weight of about 38 g/m². The stretched filled-film was adhesively laminated to about a 27 g/m² necked polypropylene spunbond fiber web with about 3 g/m² amorphous polyalphaolefin available from the Huntsman Corp. under the designation REXTAC 2730. The resulting laminate had a basis weight of about 64 g/m².

The stretched filled-film had a shrinkage of 6% (at 37° C. after 4 minutes). The laminate had a shrinkage of 0% (at 37° C. after 4 minutes), a hydrohead of 171 mbar and a WVTR of 1327 g/m²/day. The laminate had a first cycle extension tension of 461 g, a second cycle retraction tension of 111 g and a hysteresis of 76%. The peel strength of the laminate after the 50% cycle was 664 g.

EXAMPLE 2

A 100 g/m² film was made by a standard blown film process and comprised 55% by weight calcium carbonate filler coated with stearic acid and about 45% by weight polymer. The polymer comprised a blend of 25% by weight of a low density polyethylene elastomer, AFFINITY EG8200 (0.87 g/cm³, 5 MI) available from Dow Chemical Co., and 75% by weight of a linear low density polyethylene AFFINITY PL 1845 (0.91 g/cm², 3.5 MI) available from Dow Chemical Co. The film was then stretched in the machine direction 5.2 times its original length using a machine direction orienter available from Marshall and Williams Co. The slow roll was at ambient temperature and had a speed of 43 fpm, the fast roll at 190° F. and 215 fpm. The first anneal roll was at 190° F. with a speed of 205 fpm and the second anneal roll at ambient temperature with a speed of 135 fpm. The stretched film was allowed to retract over the anneal rolls, resulting in a breathable microporous film having final stretch ratio of 3.3 times its original length and a basis weight of about 35 g/m². The stretched filled-film was adhesively laminated to about a 27 g/m² necked polypropylene spunbond fiber web with about 3 g/m² amorphous polyalphaolefin available from the Huntsman Corp. under the designation REXTAC 2730. The resulting laminate had a basis weight of about 65 g/m².

The stretched filled-film had a shrinkage of 0% (at 37° C. after 4 minutes). The laminate had a shrinkage of 0% (at 37° C. after 4 minutes), a hydrohead of 192 mbar and a WVTR of 3115 g/m²/day. The laminate had a first cycle extension tension of 818 g, a second cycle retraction tension of 98 g and a hysteresis of 88%. The peel strength of the laminate after the 50% cycle was 729 g.

EXAMPLE 3

A 100 g/m² film was made by a standard blown film process and comprised 55% by weight calcium carbonate filler coated with stearic acid and about 45% by weight polymer. The polymer comprised a blend of 50% by weight of a low density polyethylene elastomer, AFFINITY EG8200 (0.87 g/cm³, 5 MI) available from Dow Chemical Co., and 50% by weight of a linear low density polyethylene AFFINITY PL 1845 (0.91 g/cm², 3.5 MI) available from Dow Chemical Co. The film was then stretched in the machine direction 5.2 times its original length using a machine direction orienter available from Marshall and Williams Co. The slow roll was at ambient temperature and had a speed of 43 fpm, the fast roll was at 160° F. and had a speed of 214 fpm. The first anneal roll was at 160° F. with a speed of 220 fpm and the second anneal roll was at ambient temperature with a speed of 135 fpm. The stretched film was allowed to retract over the anneal rolls, resulting in a breathable microporous film having final stretch ratio of 3.3 times its original length. The stretched filled-film was adhesively laminated to about a 27 g/m² necked polypropylene spunbond fiber web with about 3 g/m² amorphous polyalphaolefin available from the Huntsman Corp. under the designation REXTAC 2730. The resulting laminate had a basis weight of about 67 g/m².

The stretched filled-film had a shrinkage of 1% (at 37° C. after 4 minutes). The laminate had a shrinkage of 0% (at 37° C. after 4 minutes), a hydrohead of 183 mbar and a WVTR of 2257 g/m²/day. The laminate had a first cycle extension tension of 610 g, a second cycle retraction tension of 137 g and a hysteresis of 78%. The peel strength of the laminate after the 50% cycle was 991 g.

EXAMPLE 4

A 100 g/m² film was made by a standard blown film process and comprised 55% by weight calcium carbonate filler coated with stearic acid and about 45% by weight polymer. The polymer comprised a blend of 75% by weight of a low density polyethylene elastomer, AFFINITY EG8200 (0.87 g/cm³, 5 MI) available from Dow Chemical Co., and 25% by weight of a linear low density polyethylene AFFINITY PL 1845 (0.91 g/cm², 3.5 MI) available from Dow Chemical Co. The film was then stretched in the machine direction 6.5 times its original length using a machine direction orienter available from Marshall and Williams Co. The slow roll was at ambient temperature with a speed of 35 fpm and the fast roll was at 160° F. with a speed of 214 fpm. The first anneal roll was at 160° F. with a speed of 203 fpm and the second anneal roll was at ambient temperature with a speed of 111 fpm. The stretched film was allowed to retract over the anneal rolls, resulting in a breathable microporous film having final stretch ratio of 3.7 times its original length and a basis weight of about 35 g/m². The stretched filled-film was adhesively laminated to about a 27 g/m² necked polypropylene spunbond fiber web with about 3 g/m² amorphous polyalphaolefin available from the Huntsman Corp. under the designation REXTAC 2730. The resulting laminate had a basis weight of about 66 g/m².

The stretched filled-film had a shrinkage of 0% (at 37° C. after 4 minutes). The laminate had a shrinkage of 0% (at 37° C. after 4 minutes), a hydrohead of 172 mbar and a WVTR of 2482 g/m²/day. The laminate had a first cycle extension tension of 556 g and a second cycle retraction tension of 120 g and a hysteresis of 79%. The peel strength of the laminate after the 50% cycle was 937 g.

While various patents and other references have been incorporated herein by reference, to the extent incorporated material is inconsistent with that of the written specification the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

What is claimed is:

1. An absorbent bodily article, comprising:
   a liquid pervious liner;
   an absorbent core; and
   a thermally stable film laminate comprising a breathable film and a fibrous layer wherein said absorbent core is positioned between said liquid pervious liner and said thermally stable film laminate;
   said breathable film comprising an effective amount of filler and a thermoplastic polymer blend, said thermoplastic polymer blend comprising 30% to 70%, by weight, of a first ethylene polymer having a density below 0.89 g/cm³ and 30% to 70%, by weight, of a second ethylene polymer having a density above about 0.90 g/cm³ and wherein said film has voids adjacent said filler and further wherein said film has a WVTR of at least 300 g/m²/24 hours at 37° C. and said laminate has a heat shrinkage of less than less than 5% at 54° C.

2. The absorbent bodily article of claim 1 wherein said fibrous layer is an extensible nonwoven web.

3. The absorbent bodily article of claim 2 wherein said extensible nonwoven fabric comprises a necked nonwoven web.

4. The absorbent article of claim 3 wherein said extensible nonwoven fabric comprises a necked nonwoven web of polypropylene spunbond fibers.

5. The absorbent article of claim 2 wherein said extensible nonwoven web is an elastic nonwoven web.

6. The absorbent article of claim 1 wherein said thermoplastic polymer blend comprises about 60% to about 40%, by weight, of said first ethylene polymer.

7. The absorbent article of claim 6 wherein said second thermoplastic polymer comprises about 50%, by weight, of the second ethylene polymer.

8. The absorbent article of claim 6 wherein said breathable film has a WVTR in excess of 1500 $g/m^2/day$ at 37° C.

9. The absorbent article of claim 1 wherein the breathable film has a heat shrinkage of less than about 5% of 54° C.

10. The absorbent bodily article of claim 1 wherein said first ethylene polymer consists essentially of a copolymer of ethylene and an alpha-olefin and wherein said second ethylene polymer comprises a polyethylene polymer having a density between 0.90 $g/cm^3$ and about 0.92 $g/cm^3$.

11. A thermally stable breathable film, comprising:
   a microporous film comprising a thermoplastic polymer blend and a filler,
   said thermoplastic polymer blend comprising a first ethylene polymer having a density below 0.89 $g/cm^3$ and a second ethylene polymer having a density above about 0.90 $g/cm^3$ and wherein said first ethylene polymer and said second ethylene polymer each comprise between 25% by weight and 75% by weight of said thermoplastic polymer blend;
   said filler comprising at least 35% by weight of said microporous film; and
   wherein said microporous film has voids adjacent said filler and further wherein said film has a WVTR of at least 300 $g/m^2/24$ hours at 37° C. and less than 15% heat shrinkage at 37° C.

12. The thermally stable film of claim 11 wherein said film has a percent heat shrinkage of less than 10% at 37° C.

13. The thermally stable breathable film of claim 12 wherein said film has a WVTR in excess of 800 $g/m^2/day$ at 37° C.

14. The thermally stable film of claim 11 wherein said film has a WVTR in excess of 1500 $g/m^2/day$ at 37° C.

15. The thermally stable film of claim 14 wherein said film has a percent heat shrinkage less than about 5% at 54° C.

16. The thermally stable film of claim 11 wherein said first ethylene polymer has a density between about 0.89 $g/cm^3$ and about 0.86 $g/cm^3$.

17. The thermally stable film of claim 11 wherein said filler comprises at least about 50% by weight of said film.

18. The thermally stable film of claim 17 wherein said film has a WVTR in excess of 800 $g/m^2/day$ at 37° C.

19. The thermally stable film of claim 18 wherein said film has a heat shrinkage less than 10% at 54° C.

20. The thermally stable film of claim 18 wherein said second ethylene polymer comprises a polyethylene polymer having a density between 0.90 $g/cm^3$ and about 0.92 $g/cm^3$.

21. The thermally stable film of claim 20 wherein said first ethylene polymer consists essentially of a copolymer of ethylene and an alpha-olefin.

22. The thermally stable film of claim 11 wherein said first ethylene polymer comprises from about 40% to about 60% by weight of said thermoplastic polymer blend.

23. The thermally stable film of claim 11 wherein said first ethylene polymer comprises about 50% by weight of said thermoplastic polymer blend.

24. A thermally stable film laminate, comprising:
   a thermally stable film of claim 11; and
   a fibrous layer bonded to said laminate wherein said laminate has a shrinkage less than 5% at 54° C.

25. The thermally stable film laminate of claim 24 wherein said laminate has a shrinkage of less than about 1% of 54° C.

26. The thermally stable film laminate of claim 25 wherein said first ethylene polymer and second ethylene polymer each comprise about 50%, by weight, of the thermoplastic polymer blend.

27. The thermally stable film laminate of claim 24 wherein said laminate has a WVTR in excess of 2000 $g/m^2/24$ hours.

28. The thermally stable film laminate of claim 27 wherein said first ethylene polymer comprises from about 40% to about 60% by weight of said thermoplastic polymer blend.

29. The thermally stable film laminate of claim 24 wherein said first ethylene polymer comprises from 30% to 70% by weight of said thermoplastic polymer blend.

30. The thermally stable film laminate of claim 24 wherein said fibrous layer comprises a nonwoven web.

31. The thermally stable film laminate of claim 30 wherein said fibrous layer comprises an extensible nonwoven web.

32. The thermally stable film laminate of claim 31 wherein said fibrous layer comprises a necked nonwoven web.

33. The thermally stable film laminate of claim 24 wherein said laminate has a WVTR in excess of 800 $g/m^2/24$ hours at 37° C. and further wherein said second ethylene polymer comprises a polyethylene polymer having a density between 0.90 $g/cm^3$ and about 0.92 $g/cm^3$.

34. The thermally stable film laminate of claim 33 wherein said first ethylene polymer consists essentially of a copolymer of ethylene and an alpha-olefin.

* * * * *